(12) United States Patent
Miller et al.

(10) Patent No.: US 9,271,906 B2
(45) Date of Patent: Mar. 1, 2016

(54) ORAL COMPOSITIONS CONTAINING MICROAGGREGATES

(75) Inventors: Steven Miller, Skillman, NJ (US); Guofeng Xu, Plainsboro, NJ (US); Lin Fei, Kendall Park, NJ (US); Ying Yang, Monmouth Junction, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 118 days.

(21) Appl. No.: 13/884,030

(22) PCT Filed: Nov. 8, 2010

(86) PCT No.: PCT/US2010/055764
§ 371 (c)(1),
(2), (4) Date: May 8, 2013

(87) PCT Pub. No.: WO2012/064319
PCT Pub. Date: May 18, 2012

(65) Prior Publication Data
US 2013/0224271 A1    Aug. 29, 2013

(51) Int. Cl.
| | |
|---|---|
| *A61K 8/11* | (2006.01) |
| *A61K 8/27* | (2006.01) |
| *A61K 8/49* | (2006.01) |
| *A61K 8/73* | (2006.01) |
| *A61K 8/86* | (2006.01) |
| *A61Q 11/00* | (2006.01) |
| *A61K 8/02* | (2006.01) |

(52) U.S. Cl.
CPC .................. *A61K 8/11* (2013.01); *A61K 8/0275* (2013.01); *A61K 8/27* (2013.01); *A61K 8/4993* (2013.01); *A61K 8/731* (2013.01); *A61K 8/86* (2013.01); *A61Q 11/00* (2013.01); *A61K 2800/412* (2013.01)

(58) Field of Classification Search
CPC ....... A61K 8/27; A61K 8/4993; A61K 8/731; A61K 8/0275; A61K 8/11; A61K 8/86; A61K 2800/412; A61Q 11/00
See application file for complete search history.

(56) References Cited

U.S. PATENT DOCUMENTS

| | | |
|---|---|---|
| 3,535,421 A | 10/1970 | Briner et al. |
| 3,678,154 A | 7/1972 | Widder et al. |
| 3,696,191 A | 10/1972 | Weeks |
| 3,937,807 A | 2/1976 | Haefele |
| 3,959,458 A | 5/1976 | Agricola et al. |
| 3,991,177 A | 11/1976 | Vidra et al. |
| 4,022,880 A | 5/1977 | Vinson et al. |
| 4,051,234 A | 9/1977 | Gieske et al. |
| 4,058,595 A | 11/1977 | Colodney |
| 4,154,815 A | 5/1979 | Pader |
| 4,355,022 A | 10/1982 | Rabussay |
| 4,713,243 A | 12/1987 | Schiraldi et al. |
| 4,842,847 A | 6/1989 | Amjad |
| 4,866,161 A | 9/1989 | Sikes et al. |
| 4,885,155 A | 12/1989 | Parran, Jr. et al. |
| 4,992,420 A | 2/1991 | Neeser |
| 5,000,939 A | 3/1991 | Dring et al. |
| 5,004,597 A | 4/1991 | Majeti et al. |
| 5,059,416 A * | 10/1991 | Cherukuri et al. .............. 424/48 |
| 5,330,748 A | 7/1994 | Winston et al. |
| 5,486,350 A | 1/1996 | Norfleet et al. |
| 5,645,853 A | 7/1997 | Winston et al. |
| 5,824,292 A | 10/1998 | Carr et al. |
| 5,948,390 A * | 9/1999 | Nelson et al. ................... 424/54 |
| 5,993,834 A | 11/1999 | Shah et al. |
| 6,368,586 B1 | 4/2002 | Jacob et al. |
| 6,419,903 B1 | 7/2002 | Xu et al. |
| 6,419,906 B1 | 7/2002 | Xu et al. |
| 6,514,483 B2 | 2/2003 | Xu et al. |
| 6,592,852 B1 | 7/2003 | Ryles et al. |
| 6,669,929 B1 | 12/2003 | Boyd et al. |
| 6,989,196 B2 | 1/2006 | Chatterjee et al. |
| 7,691,413 B2 | 4/2010 | Miyamoto et al. |
| 2004/0042976 A1 | 3/2004 | Silber et al. |
| 2004/0062724 A1 | 4/2004 | Moro et al. |
| 2004/0065969 A1 | 4/2004 | Chatterjee et al. |
| 2004/0126332 A1 | 7/2004 | Boyd et al. |
| 2004/0136924 A1 | 7/2004 | Boyd et al. |
| 2007/0020201 A1 | 1/2007 | Boyd et al. |
| 2008/0281029 A1 | 11/2008 | Morvan et al. |
| 2010/0272764 A1 | 10/2010 | Latta et al. |
| 2013/0224271 A1 | 8/2013 | Miller et al. |

FOREIGN PATENT DOCUMENTS

| | | |
|---|---|---|
| CN | 1842331 | 10/2006 |
| EP | 0396232 | 11/1990 |
| EP | 0400641 | 12/1990 |
| EP | 0737470 | 10/1996 |
| EP | 0929287 | 10/2001 |
| EP | 0913144 | 11/2004 |
| FR | 2857263 | 1/2005 |
| FR | 2872169 | 12/2005 |
| JP | S40-015520 | 7/1940 |
| JP | H06-136290 | 5/1994 |
| TW | 200906444 | 2/2009 |
| WO | WO 94/26245 | 11/1994 |
| WO | WO 97/12607 | 4/1997 |
| WO | WO 2009/095423 | 8/2009 |

OTHER PUBLICATIONS

International Search Report and Written Opinion in International Application No. PCT/US10/055764, mailed Sep. 8, 2011.
Written Opinion in International Application No. PCT/US10/055764, mailed Nov. 15, 2012.

\* cited by examiner

*Primary Examiner* — Anoop Singh
*Assistant Examiner* — Doan Phan

(57) ABSTRACT

The invention relates to a composite and oral care compositions for use in the mouth to retard the accumulation of dental plaque and/or calculus. The composite is a microaggregate comprising polymer coated, surfactant stabilized particles of a substantially insoluble metal, metal salt or metal oxide, for example zinc oxide. Also methods for retarding the accumulation of dental plaque and/or calculus are provided.

13 Claims, No Drawings

ORAL COMPOSITIONS CONTAINING MICROAGGREGATES

CROSS-REFERENCE TO RELATED APPLICATIONS

This application is a National Stage Entry under 35 U.S.C. §371 of International Patent Application No. PCT/US2010/055764, filed Nov. 8, 2010, (now expired), the contents of which is hereby incorporated by reference in its entirety.

The present invention relates to oral care compositions for use in the mouth to retard the accumulation of dental plaque and/or calculus. The invention provides composites containing microaggregates of polymer coated, surfactant stabilized particles of a relatively insoluble metal, metal salt or metal oxide, for example zinc oxide, and the use of such particles in methods for retarding the accumulation of dental plaque and/or calculus.

BACKGROUND OF THE INVENTION

Dental plaque forms as a film on teeth. It is a product of microbial growth, a dense microbial layer consisting of a mass of microorganisms embedded in a matrix, which accumulates on the tooth surfaces. The microorganisms are mainly coccoidal organisms, particularly in early plaque, which, in the mouths of some persons at least, change to filamentous organisms after a few days.

Dental plaque has been observed to form following a dental prophylaxis treatment, due to bacteria which grew out of defects in the tooth enamel where they had resided and remained unaffected by the prophylaxis treatment. Plaque may form on any part of the tooth surface, and is found particularly at the gingival margin, in cracks in the enamel, and on the surface of dental calculus. The importance of giving consideration to the action of plaque on the teeth lies in the tendency of plaque to produce gingivitis and perhaps other types of periodontal disease, as well as dental caries and dental calculus. Dental plaque is a precursor of dental calculus. The latter forms from the plaque that accumulates on the teeth in the form of a hard mineralized deposit. It is particularly prone to form at the gingival margin, i.e., the junction of the tooth and gingiva. Both the bacterial and non-bacterial components of plaque are mineralized to form calculus, which comprises, in addition to mineralized bacteria, organic constituents, such as epithelial cells, live bacteria, salivary proteins, leucocytes, and crystals of substances having molecularly bound calcium and phosphorus, e.g., hydroxyapatite, octacalcium phosphate, brushite and whitlockite. Calculus, like plaque, is considered to be a prime causative factor in periodontal disease.

Therapeutic compositions containing metal oxides, including zinc oxide, within polymer particles have been described. For example, U.S. Pat. No. 6,368,586 discloses methods and compositions in which metal oxides, including zinc oxide, are incorporated into polymer microaggregates that contain a therapeutic ingredient in order to enhance the adhesion of the therapeutic polymer to mucosal surfaces. Spray drying and several alternative routes for producing polymer/metal oxide particles are disclosed. U.S. Pat. No. 7,691,413, describes composite particles containing a polyolefin-based resin having a crystallization degree of 80% or less and zinc oxide which are obtained by hot melt microencapsulation or spray cooling, a process for producing the composite particles, and cosmetics containing the composite particles.

Zinc oxide and zinc salts are known to be useful ingredients in oral care products. For example, U.S. Pat. No. 5,486,350 describes zinc compounds, including zinc oxide, among a list of anti-tartar or anti-calculus compounds useful in toothpaste. Zinc oxide has also been dispersed within a polymer matrix, cast into film and divided into strips for incorporation into oral care compositions. It is challenging to formulate zinc oxide in oral care products, however, as the particles tend to agglomerate and precipitate out of the formulation (zinc oxide is nearly insoluble in water) and/or react with other ingredients.

BRIEF SUMMARY OF THE INVENTION

The invention provides, in one embodiment, oral care compositions comprising microaggregates comprising relatively insoluble smaller particles of metal, metal salt or metal oxide, for example zinc oxide, with surfactant and a polymer coating, providing enhanced control of tartar and plaque.

In one embodiment, the particles of substantially insoluble metal, metal salt or or metal oxide, e.g., zinc oxide, are 0.1-10 microns, e.g., 0.2-2 microns, e.g., ca. 1.4 micron in average diameter, e.g., with an average surface area of 0.1-10 $m^2/g$, e.g., 0.5-5 $m^2/g$, e.g., ca. 0.7 $m^2/g$, agglomerated into microaggregates with surfactant and polymer. The microaggregates are thus clumps of greater than 5 microns, e.g., greater than 20 microns and less than 50 microns. They are formed, e.g., by blending the particles of metal or metal oxide with surfactant and polymer in the presence of a solvent, and drying, for example, spray drying. The surfactant is preferably a nonionic surfactant, for example a poly-oxyethylene sorbitan monooleate (e.g., one of the Tween series, for example Tween 80, or polyethoxylated tocopheral, for example D-alpha-tocopherol PEG 1000 succinate), which prevents particle aggregation and maintains the individual particle size. The polymer is preferably a water soluble polymer or blend of polymers, selected based on dissolution properties, which are primarily a function of chemical composition and molecular weight. The polymer preferably dissolves in saliva, to release the metal or metal oxide particles, but is stable with compounds found in oral care formulations such as toothpaste, e.g., glycerine, sorbitol and minor amounts of water. Upon use, the coated clumps break up and release the metal, metal salt or metal oxide particles at the tooth and gum surface.

In a further embodiment, methods for retarding the accumulation of dental plaque and/or calculus, using the formulations of the invention are provided.

DETAILED DESCRIPTION OF THE INVENTION

In a first embodiment, the invention provides microaggregates comprising polymer coated, surfactant stabilized particles of a substantially insoluble metal, metal salt or metal oxide, for example a microaggregate as described for use in the compositions below.

In one embodiment, the composite comprises microaggregates are incorporated into a formulation with a suitable carrier, for example an oral care composites (Composite 1.0) comprising microaggregates of polymer coated, surfactant stabilized particles of a substantially insoluble metal, metal salt or metal oxide, and a carrier, for example:

1.0.1. Composite 1.0 wherein the microaggregates are formed by spray-drying a mixture of particles, surfactant and polymer in a solvent, e.g., an aqueous solvent, e.g. selected from water and aqueous ethanol.
1.0.2. Any of the foregoing Composites wherein the substantially insoluble metal, metal salt or metal oxide is selected from zinc oxide, tin dioxide, calcium flouride, and titanium dioxide, and mixtures thereof.

1.0.3. Any of the foregoing Composites wherein the substantially insoluble metal, metal salt or metal oxide is zinc oxide.
1.0.4. Any of the foregoing Composites wherein the substantially insoluble metal, metal salt or metal oxide has a solubility in water of less than 1 mg/100 mL at 30° C.
1.0.5. Any of the foregoing Composites wherein the surfactant is a nonionic surfactant.
1.0.6. Any of the foregoing Composites wherein the surfactant is selected from polyoxyethylene-sorbitan-fatty acyl ester, a polyoxyethylene-sorbitan-fatty ether, a polyhydroxyethylene-fatty monoacyl ester, a polyhydroxyethylene-fatty diacyl ester, or a polyhydroxyethylene-fatty ether and mixtures thereof, for example polyoxyethylene sorbitan monooleates (e.g., polysorbate 20, polysorbate 40, polysorbate 60, polysorbate 65, or polysorbate 80, e.g., polysorbate 80, e.g., polyoxyethylene(20) sorbitan monooleate, for example Tween 80), or tocopheral polyethylene glycol succinates (TPGS, e.g., D-alpha-tocopherol PEG 1000 succinate), or mixtures thereof.
1.0.7. Any of the foregoing Composites wherein the polymer is a water soluble polymer.
1.0.8. Any of the foregoing Composites wherein the polymer is a mucoadhesive polymer.
1.0.9. Any of the foregoing Composites wherein the polymer is a cellulose ether.
1.0.10. Any of the foregoing Composites wherein the polymer is hydroxypropylmethylcellulose.
1.0.11. Any of the foregoing Composites wherein the microaggregates average from 1 microns to 50 microns in major dimension.
1.0.12. Any of the foregoing Composites wherein the microaggregates average greater than 5 microns in major dimension.
1.0.13. Any of the foregoing Composites wherein the microaggregates average greater than 20 microns in major dimension.
1.0.14. Any of the foregoing Composites wherein the microaggregates average from 5 microns to 30 microns in major dimension.
1.0.15. Any of the foregoing Composites wherein the microaggregates are from 10 microns to 25 microns in major dimension.
1.0.16. Any of the foregoing Composites wherein the microaggregates are generally spherical in shape and of 20 microns in major dimension.
1.0.17. Any of the foregoing Composites wherein the microaggregates are aggregates of zinc oxide particles, with a polysorbate and a cellulose ether.
1.0.18. Any of the foregoing Composites wherein the particles of substantially insoluble metal, metal salt or metal oxide, e.g., zinc oxide, are 0.1-10 microns, e.g., 0.2-2 microns, e.g., ca. 1 micron in average diameter,
1.0.19. Any of the foregoing Composites wherein the particles of substantially insoluble metal, metal salt or metal oxide have an average surface area of 0.1-10 $m^2/g$, e.g., 0.5-5 $m^2/g$, e.g., ca. 1.4 $m^2/g$.
1.0.20. Any of the foregoing Composites wherein the particles of substantially insoluble metal, metal salt or metal oxide are 1 micron on average in major dimension, with an average surface area of 1.4 $m^2/g$.
1.0.21. Any of the foregoing Composites wherein polymer dissolves in saliva upon use, but is stable with compounds found in oral care formulations such as toothpaste, e.g., glycerine, sorbitol and minor amounts of water.
1.0.22. Any of the foregoing Composites wherein the polymer is present in the microaggregate at a dry weight percent of 25 to 50%.
1.0.23. Any of the foregoing Composites wherein the particles of substantially insoluble metal, metal salt or metal oxide are present in the composite at a dry weight percent of 40 to 60%.
1.0.24. Any of the foregoing Composites further comprising a non-polymer carrier.
1.0.25. Any of the foregoing Composites wherein the microaggregate comprises a nonpolymer carrier which is propylene glycol present in the microaggregate at a dry weight percent of 5-15%.
1.0.26. Any of the foregoing Composites wherein the microaggregate comprises
 a. Water-soluble polymer, e.g. cellulose ethers, e.g., HPMC, e.g., a blend of low and high molecular weight HPMC, 30-45%
 b. Substantially insoluble metal, metal salt or metal oxide particles, e.g., zinc oxide particles, e.g., 40-60%
 c. Optionally a nonpolymer carrier, e.g., propylene glycol, e.g., 5-15%
 d. Nonpolar surfactant, e.g., polysorbate, e.g., polysorbate 80, e.g., 0.5-1%;
 e. Optionally an antifoaming agent, e.g., silicone emulsion, e.g., 0.01-0.02%
1.0.27. Any of the foregoing composites wherein the zinc material is present in an amount effective to retard, inhibit or control plaque formation with regular use.
1.0.28. Any of the foregoing composites wherein the microaggregates are present in an amount of 0.1 wt. % to 10 wt. % of the total composition weight, 1 wt. % to 7.5 wt. % of the total composition weight, for example 1 or 1.5 wt. %, 3.75 wt. %, 5 wt. %, or 7.5 wt. % of the total composition weight.
1.0.29. A composite obtained or obtainable by combining the ingredients as set forth in any of the preceding composites.

The invention also provides oral care compositions, e.g.
1.1.1. An oral care compositions comprising the composites as set forth in any of the preceding composites.
1.1.2. Any of the foregoing compositions further comprising abrasive material.
1.1.3. The immediately preceding composition wherein the abrasive material is selected from sodium bicarbonate, calcium phosphate (e.g., dicalcium phosphate dihydrate), calcium sulfate, precipitated calcium carbonate, silica (e.g., hydrated silica), iron oxide, aluminum oxide, perlite, plastic particles, e.g., polyethylene, and combinations thereof.
1.1.4. Any of the foregoing compositions further comprising an effective amount of an antibacterial agent.
1.1.5. The immediately preceding composition wherein the antibacterial agent is selected from selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions other than zinc (e.g., stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.1.6. The immediately preceding composition wherein the antibacterial agent is triclosan.

1.1.7. Any of the foregoing compositions comprising arginine, in free or orally acceptable salt form, e.g., arginine hydrochloride or arginine bicarbonate.

1.1.8. Any of the preceding compositions further comprising a soluble fluoride salt.

1.1.9. The immediately preceding composition wherein the soluble fluoride salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.1.10. Either of the two immediately preceding compositions wherein the fluoride salt is present in an amount of 0.1 wt. % to 2 wt. % of the total composition weight, e.g. 1.1% by weight of the composition.

1.1.11. Any of the preceding compositions further comprising a non-zinc anti-calculus agent, e.g., a polyphosphate, e.g., pyrophosphate, tripolyphosphate, or hexametaphosphate, e.g., in sodium salt form.

1.1.12. Any of the preceding compositions comprising at least one surfactant.

1.1.13. Any of the preceding compositions comprising at least one surfactant selected from sodium lauryl sulfate, cocamidopropyl betaine, and combinations thereof.

1.1.14. Any of the preceding compositions comprising an anionic surfactant, e.g., selected from sodium lauryl sulfate, sodium laureth sulfate, and mixtures thereof.

1.1.15. Any of the preceding compositions comprising sodium lauryl sulfate, in an amount from 0.5-3% by wt of the composition.

1.1.16. Any of the preceding compositions comprising at least one humectant.

1.1.17. Any of the preceding compositions comprising at least one humectant selected from glycerin, sorbitol and combinations thereof.

1.1.18. Any of the preceding compositions comprising at least one liquid carrier polymer, e.g selected from polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum), and combinations thereof.

1.1.19. Any of the preceding compositions comprising gum strips or fragments.

1.1.20. Any of the preceding compositions comprising flavoring, fragrance and/or coloring.

1.1.21. Any of the preceding compositions comprising water.

1.1.22. Any of the preceding compositions comprising an anti-inflammatory compound, e.g., an inhibitor of at least one of host pro-inflammatory factors selected from matrix metalloproteinases (MMP's), cyclooxygenases (COX), PGE2, interleukin 1 (IL-1), IL-1β converting enzyme (ICE), transforming growth factor β1 (TGF-β1), inducible nitric oxide synthase (iNOS), hyaluronidase, cathepsins, nuclear factor kappa B (NF-κB), and IL-1 Receptor Associated Kinase (IRAK), e,g, selected from aspirin, ketorolac, flurbiprofen, ibuprofen, naproxen, indomethacin, aspirin, ketoprofen, piroxicam, meclofenamic acid, nordihydroguaiaretic acid, and mixtures thereof.

1.1.23. Any of the preceding compositions comprising an antioxidant, e.g., selected from the group consisting of Co-enzyme Q10, PQQ, Vitamin C, Vitamin E, Vitamin A, anethole-dithiothione, and mixtures thereof.

1.1.24. Any of the preceding compositions comprising triclosan.

1.1.25. Any of the preceding compositions comprising triclosan in an amount of 0.01 to 1 wt. percent of the total composition weight.

1.1.26. Any of the preceding compositions comprising triclosan in an amount of 0.3% of the total composition weight.

1.1.27. Any of the preceding compositions comprising a whitening agent.

1.1.28. Any of the preceding compositions comprising a whitening agent selected from a whitening active selected from the group consisting of peroxides, metal chlorites, perborates, percarbonates, peroxyacids, hypochlorites, and combinations thereof 1.1.29. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.1.30. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate.

1.1.31. Any of the preceding compositions further comprising a soluble calcium salt, e.g., selected from calcium sulfate, calcium chloride, calcium nitrate, calcium acetate, calcium lactate, and combinations thereof.

1.1.32. Any of the preceding compositions further comprising an agent that interferes with or prevents bacterial attachment, e.g., solbrol or chitosan.

1.1.33. Any of the preceding compositions further comprising a physiologically acceptable potassium salt, e.g., potassium nitrate, potassium citrate, or potassium chloride, in an amount effective to reduce dentinal sensitivity.

1.1.34. Any of the preceding compositions effective upon application to the oral cavity, e.g., with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) reduce dry mouth, (xiii) clean the teeth and oral cavity (xiv) reduce erosion, (xv) whiten teeth, and/or (xvi) immunize the teeth against cariogenic bacteria 1.1.35. Any of the preceding compositions further comprising an antifoaming agent.

1.1.36. Any of the foregoing compositions, wherein the composition is toothpaste.

1.1.37. Any of the preceding Composites wherein the composition is a toothpaste optionally further comprising one or more of one or more of water, abrasives, surfactants, foaming agents, vitamins, polymers, enzymes, humectants, thickeners, antimicrobial agents, preservatives, flavorings, colorings and/or combinations thereof.

1.1.38. Any of the foregoing Composites which is a toothpaste comprising microaggregates comprising zinc oxide particles, wherein the agglomerates are 5 to 50 microns in major dimension, the individual particles are 1 micron on average in major dimension, with an average surface area of 1.4 $m^2$/g, and the polymer coating the microaggregates has been applied by spray drying and comprises hydroxypropylmethylcellulose.

1.1.39. A composition obtained or obtainable by combining the ingredients as set forth in any of the preceding compositions.

The invention also provides methods, e.g.

1.2.1. A method for retarding the accumulation of dental plaque and/or calculus comprising contacting oral surfaces with composites comprising microaggregates of polymer coated, surfactant stabilized particles of a substantially insoluble metal, metal salt or metal oxide, e.g., using any of the foregoing Compositions 1.0 et seq., e.g., by brushing the teeth and gums with a composition comprising the microaggregates.

1.2.2. A method to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) reduce dry mouth, (xiii) clean the teeth and oral cavity (xiv) reduce erosion, (xv) whiten teeth, and/or (xvi) immunize the teeth against cariogenic bacteria, comprising contacting oral surfaces with microaggregates comprising polymer coated, surfactant stabilized particles of a substantially insoluble metal, metal salt or metal oxide, e.g., using any of the foregoing Compositions 1.0 et seq.

1.2.3. A method of making microaggregates comprising polymer coated, surfactant stabilized particles of a substantially insoluble metal, metal salt or metal oxide comprising mixing the ingredients as described above, e.g., mixing the following ingredients
a. Water-soluble polymer, e.g. cellulose ethers, e.g., HPMC, e.g., a blend of low and high molecular weight HPMC, 30-45%;
b. Substantially insoluble metal, metal salt or metal oxide particles, e.g., zinc oxide particles, e.g., 40-60%;
c. Nonpolar surfactant, e.g., polysorbate, e.g., polysorbate 80, e.g., 0.5-1%;
d. Optionally a nonpolymer carrier, e.g., propylene glycol, e.g., 5-15%;
e. Optionally an antifoaming agent, e.g., silicone emulsion, e.g., 0.01-0.02% with a suitable solvent or carrier, e.g., water and/or ethanol;
spray-drying the mixture; and
recovering the microaggregates thus obtained.

In one embodiment, the substantially insoluble metal, metal salt or metal oxide particles, e.g., zinc oxide powder, are mixed with various coating solutions using continuous agitation to form homogenous suspensions suitable for pumping and spraying. The coating solution may contain polymers, co-solvents, surfactants, spreading agents, salts, or other additives to adjust performance.

Polymers:

The polymers useful in coating the zinc particle aggregates generally include any of the polymers typically useful in oral care compositions, as discussed below. In one embodiment, mucoadhesive polymers are preferred, as they can extend the effective contact time between the particles and oral tissues. For example, the microaggregates may utilize hydrophilic polymers☐ or hydrogels. In the large classes of hydrophilic polymers those containing carboxylic groups exhibit the best mucoadhesive properties, poly vinyl pyrrolidone (PVP), Methyl cellulose (MC), Sodium carboxy methylcellulose (SCMC) Hydroxy propyl cellulose (HPC) and other cellulose derivatives, such as hydroxypropylmethyl cellulose (HPMC). Hyrogels are the class of polymeric biomaterial that swell by absorbing water, interacting by means of adhesion with the mucus that covers epithelia i.e. an anionic group—Carbopol, polyacrylates and their crosslinked modifications; a cationic group—chitosan and its derivatives; or a neutral group—Eudragit—NE30D etc.

The oral care compositions of the invention thus may include one or more polymers, such as polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of 30,000 to 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of 1,000 to 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

Useful polymers include hydrophilic and hydrophobic polymers. In some embodiments, the polymer is soluble in a solvent, such as water. A water-soluble polymer that dissolves during exposure to water and application of physical force during use (such as during tooth brushing or scrubbing with a brush or pad) is desirable. In some embodiments, the polymer is insoluble but breakable in water by being dispersible, i.e., the polymer breaks down into small fragments as a result of the application of mechanical or shear force. In some embodiments, a polymer is insoluble but swellable. Where the polymer does not fully break down during use, it may be a water-repellant polymer or an aqueous-stable hydrophilic polymer such as certain types of cellulose, e.g., paper. Examples of useful are described in U.S. Pat. No. 4,713,243 to Schiraldi et al., U.S. Pat. Nos. 6,419,903, 6,419,906, 6,514,483 all to Xu, and U.S. Pat. No. 6,669,929 to Boyd et al.; United States Patent Publication Nos. 2004/0126332, 2004/0136924, and 2004/0042976 all to Boyd et al., and 2004/0062724 to Moro et al.

Preferably, the polymers are selected to provide at least one of the following: (1) a desired stability of the microparticle in the carrier, (2) a desired rate of disintegration of the polymers during use of the composition, or (3) a desired rate of exposure of the particles during use of the composition.

In preferred embodiments, the polymer coating is water-soluble, comprising, for example, a water soluble polymer, water dispersible polymer or water insoluble polymer with an optional water-soluble filler. The relative amounts of water-insoluble polymer, water-soluble polymer or optional water-soluble filler may be selected to release an amount of active ingredient proportional to how vigorously or how long the composition is used, e.g., by brushing, scrubbing, or other mechanical action during use of the aqueous composition.

In a particular embodiment the water soluble polymer is a cellulose ether polymer, such as hydroxylalkyl alkyl cellulose, including hydroxypropyl methyl cellulose (HPMC) commercially available from the Dow Chemical Company of Midland, Mich., United States of America, as METHOCEL® products, including, for example, METHOCEL® E5, METHOCEL® E5 LV, METHOCEL® E50, METHOCEL® E15, and METHOCEL® K100, hydroxypropyl cellulose (HPC), hydroxyethyl cellulose (HEC), methyl cellulose (MC), carboxymethyl cellulose (CMC), and mixtures thereof. Other useful polymers include polyvinylpyrrolidone (PVP), which can have a weight average molecular weight of 100,000 or more and up to 1.5 million, vinyl acetate, polyvinylpyrrolidone-vinyl acetate copolymers such as KOLLIDON® VA64 (available from BASF, 60:40 by weight vinyl pyrrolidone) and PLASDONE® S630 PVP (available from International Specialty Products, Wayne, N.J., United States of America, 60:40 by weight vinyl pyrrolidone:vinyl acetate), ethylene oxide graft copolymers of PVA such as KOLLICOAT® IR (available from BASF, 75% by weight PVA, 25% by weight polyethylene glycol graft, polyvinyl alcohol (PVA), acrylates and polyacrylic acid, including polyacrylate polymer, cross-linked polyacrylate polymer, cross-linked polyacrylic acid (e.g., CARBOPOL®), vinylcaprolactam/sodium acrylate polymers, methacrylates, maleic poly vinylalkyl ether-maleic acid copolymer (e.g., GANTREZ®), vinyl acetate and crotonic acid copolymers, polyacrylamide, poly (2-acrylamido-2-methylpropane sulfonate), terpolymers of acrylomethyl propyl sulphonic acidlmethylacrylate/styrene monomers, phosphonate styrene polymers, polyethylene phosphonate, polybutene phosphonate, polystyrene, polyvinylphosphonates, polyalkylenes, polyalkylene oxides, including polyethylene oxide, i.e. polyethylene glycol, and carboxy vinyl polymer. As appreciated by a skilled artisan, the film may comprise derivatives, copolymers, and further mixtures of such polymers as well.

The polymer may comprise a mix of water soluble and water insoluble polymers, provided that the particles are released on application. Useful water-insoluble polymers include polymers soluble in at least one organic solvent; for example, acrylic copolymers (where carboxylic acid functionality has not been neutralized), cross-linked poly(vinyl pyrrolidone), for example KOLLIDON® CL or CL-M available from BASF, poly(vinyl acetate) (PVAc), certain cellulose derivatives such as cellulose acetate, cellulose nitrate, alkyl cellulose such as ethyl cellulose, butyl cellulose, and isopropyl cellulose, cellulose acetate phthalate, shellac, ethylene-vinyl acetate copolymers, vinyl acetate homopolymer, silicone polymer (e.g., dimethylsilicone), polymethyl methacrylate (PMMA), polymers insoluble in organic solvents, such as cellulose, polyethylene, polypropylene, polyesters, polyurethane and nylon, natural or synthetic rubber, and mixtures thereof. An example of a suitable, film-forming acrylic copolymer is LUVIMER® 30E, a 30% by weight solution in ethanol of a tert-butyl acrylate/ethyl acrylate/methyacrylic acid copolymer commercially available from BASF (Florham Park, N.J., United States of America). The water-insoluble polymers may be prepared as dispersions (e.g., by emulsion polymerization) and may be stabilized with suitable emulsifiers. One useful PVAc emulsion, for example, is KOLLICOAT® SR 30D, a 30 weight % dispersion of PVAc in water stabilized with 2.7 weight percent PVP and 0.3% sodium lauryl sulfate. An example of an acrylic copolymer dispersion is KOLLICOAT® EMM 30D, a 30% by weight aqueous dispersion of an ethyl acrylate:methyl methacrylate copolymer (weight ratio of ethyl acrylate to methyl methacrylate approximately 2 to 1) with a reported average molecular weight of 800,000, available from BASF.

Other useful polymers or water-soluble fillers include, without limitation, natural gums such as sodium alginate, carrageenan, xanthan gum, gum acacia, Arabic gum, guar gum, pullulan, agar, chitin, chitosan, pectin, karaya gum, zein, hordein, oliadin, locust bean gum, tragacantha and other polysaccharides; starches such as maltodextrin, amylose, high amylose starch, corn starch, potato starch, rice starch, tapioca starch, pea starch, sweet potato starch, barley starch, wheat starch, waxy corn starch, modified starch (e.g., hydroxypropylated high amylose starch), dextrin, levan, elsinan and gluten; and proteins such as collagen, whey protein isolate, casein, milk protein, soy protein, keratin, and gelatin. The coating polymer may further include dispersible or swellable fillers such as modified starch, alginate esters, divalent or multivalent ion salts of alginates.

Further non-limiting examples of water insoluble polymers include cellulose acetate, cellulose nitrate, ethylene-vinyl acetate copolymers, vinyl acetate homopolymer, ethyl cellulose, butyl cellulose, isopropyl cellulose, shellac, hydrophobic silicone polymer (e.g., dimethylsilicone), PMMA (polymethyl methacrylate), cellulose acetate phthalate and natural or synthetic rubber; polymers insoluble in organic solvents, such as cellulose, polyethylene, polypropylene, polyesters, polyurethane and nylon.

In an aqueous composition, the relative amounts of water-soluble polymer and water-insoluble and/or partially water-soluble polymer in the polymer coat are preferably such that the coating is storage-stable in an aqueous composition but disintegrates during use of the composition. In various embodiments, the coating includes an amount of water-soluble polymer that is 0.1% to 90%, 1% to 80%, 5% to 70%, 9% to 50% or 10% to 40°% by weight of the coating. In addition to, or instead of, the water-soluble polymer(s), the coating may include partially water-insoluble or water-swellable polymers in amounts of 0.1% to 50% by weight of the coating, preferably 1% to 10 weight %. In various embodiments, a method of stabilizing hydrophilic coatings in an aqueous carrier environment uses water-soluble and water-insoluble materials in the coating that are balanced for stability while stored in the product carrier, but disintegrate upon use to release the active ingredient contained therein.

In preparing the coating solution, the appropriate solvents and co-solvents for the chosen polymer(s) should be selected, according to the general knowledge in the art, to produce a flowable film-forming coating solution at the operating temperatures.

The surfactants used to stabilize the particles in the microaggregates are preferably nonpolar surfactants, or any surfactant capable of inhibiting aggregation of the particles prior to formation of the microaggregates or after application. Suitable polymers thus include, for example, polyoxyethylene-sorbitan-fatty acyl ester, a polyoxyethylene-sorbitan-fatty ether, a polyhydroxyethylene-fatty monoacyl ester, a polyhydroxyethylene-fatty diacyl ester, or a polyhydroxyethylene-fatty ether and mixtures thereof, for example polyoxyethylene sorbitan monooleates (e.g., polysorbate 20, polysorbate 40, polysorbate 60, polysorbate 65, or polysorbate 80, e.g., polysorbate 80, e.g., polyoxyethylene(20) sorbitan monooleate, for example Tween 80), as well s tocopheral polyethylene glycol succinates (TPGS, e.g., D-alpha-tocopherol PEG 1000 succinate), and mixtures of any of the foregoing.

Oral Care Formulations:

The microaggregates of the invention can be formulated in to oral care compositions according to known methods. A toothpaste containing the microaggregates is particularly preferred.

Fluoride Ion Sources:

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference.

Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof.

In certain embodiments, the oral care composition of the invention may also contain a source of fluoride ions or fluorine-providing ingredient in amounts sufficient to supply 25 ppm to 25,000 ppm of fluoride ions, generally at least 500 ppm, e.g., 500 to 2000 ppm, e.g., 1000 to 1600 ppm, e.g., 1450 ppm. The appropriate level of fluoride will depend on the particular application. A toothpaste for general consumer use would typically have 1000 to 1500 ppm, with pediatric toothpaste having somewhat less. A dentifrice or coating for professional application could have as much as 5,000 or even 25,000 ppm fluoride.

Fluoride ion sources may be added to the compositions of the invention at a level of 0.01 wt. % to 10 wt. % in one embodiment or 0.03 wt. % to 5 wt. %, and in another embodiment 0.1 wt. % to 1 wt. % by weight of the composition in another embodiment. Weights of fluoride salts to provide the appropriate level of fluoride ion will obviously vary based on the weight of the counter ion in the salt.

Where the composition comprises calcium bicarbonate, sodium monofluorophosphate is preferred to sodium fluoride for stability reasons.

Abrasives:

The microaggregates of the invention may by incorporated into a dentifrice together with abrasive materials, for example natural calcium carbonate, precipitated calcium carbonate, calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate, and/or silica abrasives such as precipitated silicas having a mean particle size of up to 20 μm, such as Zeodent 115®, marketed by J. M. Huber, sodium metaphosphate, potassium metaphosphate, aluminum silicate, calcined alumina, bentonite or other siliceous materials, or combinations thereof.

Foaming Agents:

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of 200,000 to 7,000,000. In one embodiment the molecular weight will be 600,000 to 2,000,000 and in another embodiment 800,000 to 1,000,000. Polyox® is the trade name for the high molecular weight polyoxyethylene produced by Union Carbide. The polyoxyethylene may be present in an amount of 1% to 90%, in one embodiment 5% to 50% and in another embodiment 10% to 20% by weight of the oral care carrier component of the oral care compositions of the present invention. The dosage of foaming agent in the oral care composition (i.e., a single dose) is 0.01 to 0.9% by weight, 0.05 to 0.5% by weight, and in another embodiment 0.1 to 0.2% by weight.

Surfactants:

Another agent optionally included in the oral care composition of the invention is a surfactant or a mixture of compatible surfactants. Suitable surfactants are those which are reasonably stable throughout a wide pH range, for example, anionic, cationic, nonionic or zwitterionic surfactants. Suitable surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference.

In certain embodiments, the anionic surfactants useful herein include the water-soluble salts of alkyl sulfates having 10 to 18 carbon atoms in the alkyl radical and the water-soluble salts of sulfonated monoglycerides of fatty acids having 10 to 18 carbon atoms. Sodium lauryl sulfate, sodium lauroyl sarcosinate and sodium coconut monoglyceride sulfonates are examples of anionic surfactants of this type. Mixtures of anionic surfactants may also be utilized.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof.

Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

In certain embodiments, zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains 8 to 18 carbon atoms and one contains an anionic water-solubilizing group, e.g., carboxy, sulfonate, sulfate, phosphate or phosphonate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof. In a particular embodiment, the composition of the Invention comprises an anionic surfactant, e.g., sodium lauryl sulfate.

The surfactant or mixtures of compatible surfactants can be present in the compositions of the present invention in 0.1% to 5.0%, in another embodiment 0.3% to 3.0% and in another embodiment 0.5% to 2.0% by weight of the total composition.

Flavoring Agents:

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.1 to 5% by weight and 0.5 to 1.5% by weight. The dosage of flavoring agent in the individual oral care composition dosage (i.e., a single dose) is 0.001 to 0.05% by weight and in another embodiment 0.005 to 0.015% by weight.

Chelating Agents:

The oral care compositions of the invention also may optionally include one or more chelating agents able to complex calcium found in the cell walls of the bacteria. Binding of this calcium weakens the bacterial cell wall and augments bacterial lysis.

Another group of agents suitable for use as chelating agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 1.0 wt. % pyrophosphate ions, 1.5 wt. % to 6 wt. %, 3.5 wt. % to 6 wt. % of such ions.

Thickening Agents:

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of 0.5% to 5.0% by weight of the total composition are used.

Enzymes:

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. No. 4,992,420; U.S. Pat. No. 4,355,022; U.S. Pat. No. 4,154,815; U.S. Pat. No. 4,058,595; U.S. Pat. No. 3,991,177; and U.S. Pat. No. 3,696,191 all incorporated herein by reference. An enzyme of a mixture of several compatible enzymes in the current invention constitutes 0.002% to 2.0% in one embodiment or 0.05% to 1.5% in another embodiment or in yet another embodiment 0.1% to 0.5%.

Water:

Water may also be present in the oral compositions of the invention. Water, employed in the preparation of commercial oral compositions should be deionized and free of organic impurities. Water commonly makes up the balance of the compositions and includes 10% to 90%, 20% to 60% or 10% to 30% by weight of the oral compositions. This amount of water includes the free water which is added plus that amount which is introduced with other materials such as with sorbitol or any components of the invention.

Humectants:

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes 15% to 70% in one embodiment or 30% to 65% in another embodiment by weight of the dentifrice composition. Suitable humectants include edible polyhydric alcohols such as glycerine, sorbitol, xylitol, propylene glycol as well as other polyols and mixtures of these humectants. Mixtures of glycerin and sorbitol may be used in certain embodiments as the humectant component of the toothpaste compositions herein.

dal or polymodal distributions also occur, in which more than one representative size class is present within the resulting material. Typically, the larger particles representative of the population are larger than 5 µm along a major axis or diameter. Preferably, microaggregates range between about 5 µm and 50 µm in size.

One skilled in the art is familiar with the technique, and descriptions of useful processes are readily available, for example in U.S. Pat. No. 6,368,586, mentioned above, which also provides informative descriptions of alternate routes for producing finished free-flowing particles containing metal oxide and polymer, all of which are hereby incorporated by reference as if set forth at length herein.

Example

Formulations are prepared according to the Mixing Procedure in the proportions identified on the following Table 1.

TABLE 1

| | Sample # | | | | | | | | |
|---|---|---|---|---|---|---|---|---|---|
| | 1 | | 2 | | 3 batch size | | 4 | | 5 |
| | 120 % (Dry %) | gram | 120 % (Dry %) | gram | 150 % (Dry %) | gram | 120 % (Dry %) | gram | 120 % (Dry %) | gram |
| HPMC E5 | 6.33 (17.39) | 7.59 | 9.03 (28.89) | 10.84 | 3.01 (8.28) | 4.52 | 9.03 (24.83) | 10.84 | 3.01 (9.63) | 3.61 |
| HPMC E50 | 5.71 (15.69) | 6.85 | 3.01 (9.63) | 3.61 | 9.03 (24.83) | 13.55 | 3.01 (8.28) | 3.61 | 9.03 (28.89) | 10.84 |
| ZnO | 18.89 (51.96) | 22.67 | 18.89 (60.46) | 22.67 | 18.89 (51.95) | 28.34 | 18.89 (51.95) | 22.67 | 18.89 (60.46) | 22.67 |
| PG | 5.12 (14.08) | 6.14 | 0 (0) | 0 | 5.12 (14.08) | 7.68 | 5.12 (14.08) | 6.14 | 0 (0) | 0 |
| Tween80 | 0.31 (0.85) | 0.37 | 0.31 (0.99) | 0.37 | 0.31 (0.85) | 0.46 | 0.31 (0.85) | 0.37 | 0.31 (0.99) | 0.37 |
| FG-10 | 0.01 (0.02) | 0.01 | 0.01 (0.03) | 0.01 | 0.01 (0.02) | 0.01 | 0.01 (0.02) | 0.01 | 0.01 (0.03) | 0.01 |
| EtOH | 5.63 | 6.75 | 5.63 | 6.76 | 5.63 | 8.45 | 5.63 | 6.76 | 5.63 | 6.76 |
| Water | 58.01 | 69.61 | 58.01 | 75.74 | 58.01 | 87 | 58.01 | 69.6 | 58.01 | 75.74 |
| Total | 100 | | 100 | | 100 | | 100 | | 100 | |

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Spray Drying:

Suspensions of relatively insoluble metal, metal salt or metal oxide particles, e.g., zinc oxide powder, surfactant, and coating polymer are passed through a spray dryer to generate dried polymer coated microaggregates. Spray drying is a well established technique in industry that is useful for producing free flowing dry particulate products from wet starting materials. Methods of using spray drying techniques are well known in the art. In general, the particle sizes produced are influenced by the major particle sizes present in the wet feed, and typically range from 1 µm to 50 µm, measured along a major dimensional axis, usually from 5 microns to 30 microns in major dimension; preferably from 10 microns to 25 microns in major dimension. A particularly preferred embodiment contains spray dried polymer coated zinc oxide particles that are generally spherical in shape and of 20 microns in major dimension.

In addition, as with most materials, the resulting particle sizes will vary across a particle size distribution. The particle size distribution obtained is often unimodal, however, bimo- Further formulations are made using ingredients as set forth in Table 2:

TABLE 2

| | Sample # | | | |
|---|---|---|---|---|
| | 8 | | 9 batch size | |
| | 120 % (Dry %) | gram | 120 % (Dry %) | gram |
| HPMC E5 | 12.03 (33.09) | 14.44 | 15.46 (42.52) | 18.55 |
| HPMC E50 | 0 (0) | 0 | 0 (0) | 0 |
| ZnO | 18.89 (51.96) | 22.67 | 15.46 (42.52) | 18.56 |
| PG | 5.12 (14.08) | 6.14 | 5.12 (14.08) | 6.14 |
| Tween80 | 0.31 (0.85) | 0.37 | 0.31 (0.85) | 0.371 |
| FG-10 | 0.01 (0.02) | 0.01 | 0.01 (0.02) | 0.0099 |
| EtOH | 5.63 | 6.75 | 5.63 | 6.75 |
| Water | 58.01 | 69.61 | 58.01 | 69.61 |
| Total | 100 | 120 | 100 | 120 |
| EtOH/H2O (5.63/58) | | 60 | | 60 |
| Viscosity | | 430 | | 600 |
| Yield | | 43% | | 50% |

Shortened ingredient names appearing on the foregoing tables refer to the specific ingredients here identified: HPMC E5=hydroxypropylmethylcellulose HPMC E50=hydroxypropylmethyl cellulose E50, ZnO=zinc oxide powder, average particle diameter 1 micron, PG=Propylene Glycol, Tween 80=polysorbate surfactant, (available from ICI Americas Inc.), FG-10=antifoam emulsion (available from Dow Corning), EtOH=Ethanol.

Mixing Procedure:

The HPMC E5, HPMC E50, PG and Tween 80 are dissolved in water. Then ZnO powder is added to the wet ingredients, followed by ethanol. The materials were blended until a homogenous mixture is observed.

Spray Drying Procedure

The resulting wet formulations are fed into a Buchi B-290 spray dryer, configured at Inlet temperature=170° C., Outlet temperature=99-100° C., Aspiration=100%, Air flow=40, Feeding rate=30% (7.2 mL/min).

The spray dried material obtained is observed using Scanning Electron Microscopy and contained a bimodal particle distribution consisting of large spherical polymer coated ZnO particles ~20 μm in diameter and irregular shaped particles of dried polymer ~5 μm in major dimension.

Small amounts of Samples 1-6 of spray dried material were placed on a glass slide. 50 μL of glycerine/water (1:4) was added to each slide. Viscosity of glycerin/water was 1.76 cp/mPa*s. The particles were observed under microscope (4× magnification). The time was recorded at which the sample disintegrated fastest and also the time when the disintegration is 50%, 75%, 90% and 99% completed. The times are recorded in TABLE 3.

TABLE 3

| Sample ID | Ratio E5/E50 | highest dissolving rate | 50% dissolved | 75% dissolved | 90% dissolved | 99% dissolved |
|---|---|---|---|---|---|---|
| | | | Minutes | | | |
| #1 | 1.11 | 1.5 | | 3 | 5 | 11 |
| #2 | 1.11 | 1.83 | 3 | 4.5 | 6.5 | 11 |
| #3 | 0.33 | 1.58 | 2.83 | 5 | 12 | 30 |
| #4 | 3 | 1 | 1.33 | 2.5 | 5 | 6.33 |
| #5 | 3 | 1.25 | 2 | 3.25 | 5 | 6 |
| #6 | 0.33 | 1.67 | 3.33 | 6.5 | 15 | 24 |

Uptake Method

VITRO-SKIN® is a testing substrate that effectively mimics the surface properties of human skin. It contains both optimized protein and lipid components and is designed to have topography, pH, critical surface tension and ionic strength similar to human skin. Vitro-Skin is cut into squares to match the size of HAP disks (12.4×12.4 mm=½×½ inch). The samples are rinsed three times with hexanes, and then incubated overnight in 1 mL of saliva at 37° C. (each measurement in triplicate Two suspensions are prepared in deionized water, containing 1% suspension of spray dried ZnO, and 0.5% suspension of ZnO powder, repectively. Saliva was aspirated from the tubes with Vitro-Skin. A 2 mL aliquot of ZnO suspension is added into each tube. The slurry is aspirated from the tubes and rinsed with 5 mL of water (vortex 1×10 sec.). The tubes are rinsed again with 5 mL of water (vortex 1×10 sec.). The Vitro Skin samples are transferred into a new tube, and vortex rinsed in 1 mL of HCl (1 Molar) for 30 seconds. The 4 mL of DI water is added and allowed to sit for 2 hours, vortexing occasionally. The solution is then analyzed by atomic spectrometry to measure concentration of zinc. The amount of ZnO uptake on the samples is measured on a microgram/sheet basis and the results are shown in TABLE 4.

TABLE 4

| Sample ID | μg of ZnO per sheet | Average | Std. Dev. |
|---|---|---|---|
| ZnO powder 1 | 122.4795 | 107.7 | 13.8 |
| ZnO powder 2 | 95.15808 | | |
| ZnO powder 3 | 105.4269 | | |
| ZnO SprayDry 1 | 183.5947 | 181.4 | 18.6 |
| ZnO SprayDry 2 | 161.8123 | | |
| ZnO SprayDry 3 | 198.8424 | | |

ZnO Uptake on Vitro Skin is a simplified liquid dentifrice model. The spray dried ZnO powder is surprisingly more effective in terms of ZnO uptake on VitroSkin.

In Vitro Efficacy Test

The efficacy of samples are tested and rated on microbial zone inhibition. The spray dried ZnO performed better than untreated ZnO powder.

What is claimed is:

1. A composite comprising microaggregates of polymer coated, nonionic surfactant stabilized particles of a substantially insoluble metal, metal salt or metal oxide, wherein the polymer is a water-soluble polymer or blend of water soluble polymers;
   wherein the microaggregates average from 5 microns to 50 microns in major dimension;
   wherein the non-ionic surfactant is selected from the group consisting of polyoxyethylene-sorbitan-fatty acyl ester, a polyoxyethylene-sorbitan-fatty ether, a polyhydroxyethylene-fatty monoacyl ester, a polyhydroxyethylene-fatty diacyl ester, and a polyhydroxyethylene-fatty ether; and
   wherein the substantially insoluble metal, metal salt or metal oxide is selected from the group consisting of: zinc oxide, tin dioxide, calcium fluoride, titanium dioxide, and mixtures thereof.

2. The composite of claim 1, wherein the polymer comprises hydroxypropylmethylcellulose.

3. The composite of claim 2 wherein the surfactant comprises polysorbate 80.

4. The composite of claim 1, wherein the microaggregates are formed by spray drying a mixture comprising zinc oxide particles, surfactant and water-soluble polymer.

5. The composite of claim 1, wherein the microaggregates comprise zinc oxide particles coated with a cellulose ether polymer, are generally spherical in shape, and average 20 microns in major dimension.

6. An oral care composition comprising a plurality of composites according to claim 1.

7. The composition of claim 6, wherein the composition is a toothpaste.

8. A method for retarding the accumulation of dental plaque and/or calculus comprising contacting oral surfaces with a plurality of composites according to claim 1.

9. A method of making a composite comprising microaggregates of polymer coated, nonionic surfactant stabilized particles of a substantially insoluble metal, metal salt or metal oxide, wherein the polymer is a water-soluble polymer or blend of water soluble polymers according to claim 1, comprising
   mixing a coating polymer and a substantially insoluble metal, metal salt or metal oxide and a surfactant, optionally together with a nonpolymer carrier and/or an antifoaming agent, in a suitable solvent or carrier,
   spray-drying the mixture; and
   recovering the composite thus obtained, wherein the polymer is a water-soluble polymer or blend of water soluble polymers;

wherein the microaggregates average from 5 microns to 50 microns in major dimension;

wherein the non-ionic surfactant is selected from the group consisting of polyoxyethylene-sorbitan-fatty acyl ester, a polyoxyethylene-sorbitan-fatty ether, a polyhydroxyethylene-fatty monoacyl ester, a polyhydroxyethylene-fatty diacyl ester, and a polyhydroxyethylene-fatty ether; and wherein the substantially insoluble metal, metal salt or metal oxide is selected from the group consisting of: zinc oxide, tin dioxide, calcium fluoride, titanium dioxide, and mixtures thereof.

10. The composite of claim 3, wherein the microaggregates are formed by spray drying a mixture comprising zinc oxide particles, surfactant and water-soluble polymer.

11. The composite of claim 10, wherein the microaggregates comprise zinc oxide particles coated with a cellulose ether polymer, are generally spherical in shape, and average 20 microns in major dimension.

12. The composite of claim 1, wherein the substantially insoluble metal, metal salt or metal oxide is zinc oxide.

13. The composite of claim 12, wherein the surfactant is polysorbate 80.

\* \* \* \* \*